United States Patent
Lutz

(10) Patent No.: US 8,053,228 B2
(45) Date of Patent: Nov. 8, 2011

(54) BIOREACTOR COMPRISING A RETAINING SYSTEM

(75) Inventor: Peter Lutz, Unterföhring (DE)

(73) Assignee: Bekon Energy Technologies GmbH & Co., KG, Unterfohring (DE)

( * ) Notice: Subject to any disclaimer, the term of this patent is extended or adjusted under 35 U.S.C. 154(b) by 183 days.

(21) Appl. No.: 12/066,071

(22) PCT Filed: Sep. 8, 2006

(86) PCT No.: PCT/EP2006/008794
§ 371 (c)(1),
(2), (4) Date: Oct. 10, 2008

(87) PCT Pub. No.: WO2007/028642
PCT Pub. Date: Mar. 15, 2007

(65) Prior Publication Data
US 2009/0155892 A1    Jun. 18, 2009

(30) Foreign Application Priority Data
Sep. 8, 2005 (DE) .................. 20 2005 014 176 U

(51) Int. Cl.
*C12M 1/00* (2006.01)
*C12M 1/12* (2006.01)
*C12M 1/107* (2006.01)
*C02F 3/00* (2006.01)
*B01D 37/00* (2006.01)

(52) U.S. Cl. ............... 435/290.1; 435/289.1; 435/297.1; 210/601; 210/767

(58) Field of Classification Search ............... 435/297.1, 435/289.1, 290.1; 210/601, 767
See application file for complete search history.

(56) References Cited

U.S. PATENT DOCUMENTS
5,403,742 A * 4/1995 Freeman ................. 435/298.1
(Continued)

FOREIGN PATENT DOCUMENTS
DE    37 19 564 A1    12/1988
(Continued)

OTHER PUBLICATIONS
English translation of WO 02/06439, Jan. 2002.*
(Continued)

*Primary Examiner* — Michael Marcheschi
*Assistant Examiner* — Gautam Prakash
(74) *Attorney, Agent, or Firm* — Morrison & Foerster LLP

(57) ABSTRACT

Disclosed is a bioreactor in which a supporting wall (100) or a retaining mechanism (100) that represents pressure relief for a gas-tightly embodied flap is provided behind the flap (14) used for filling and emptying the bioreactor while percolate is prevented from accumulating between the gas-tight flap and the retaining mechanism. The gas-tightly closable flap, which has a sufficiently large size, makes it easy to fill biomass into the container and remove the remaining biomass following the methanation process. The biomass applies substantial or at least a certain amount of pressure to the retaining system when the container is closed, whereby the flap is relieved of the load and can be embodied in a light and accurately sealing manner. A device (22) for draining percolating juice or percolate is disposed in the floor and/or the walls of the bioreactor between the flap and the retaining system such that percolating juice is prevented from accumulating in the zone between the flap and the retaining system or percolate located there can be pumped off before the flap is opened.

4 Claims, 4 Drawing Sheets

U.S. PATENT DOCUMENTS

| | | | |
|---|---|---|---|
| 6,254,775 B1 * | 7/2001 | McElvaney | 210/603 |
| 6,569,332 B2 | 5/2003 | Ainsworth et al. | |
| 6,699,708 B1 * | 3/2004 | Muller et al. | 435/262 |

FOREIGN PATENT DOCUMENTS

| | | |
|---|---|---|
| DE | 44 44 462 A1 | 6/1996 |
| DE | 20203533 U1 | 11/2002 |
| DE | 101 29 718 A1 | 2/2003 |
| DE | 201 21 701 U | 3/2003 |
| DE | 102 57 849 A1 | 7/2004 |
| DE | 10302658 A1 | 7/2004 |
| DE | 20319847 U1 | 6/2005 |
| DE | 202005014176 U | 10/2006 |
| EP | 0023176 A2 | 1/1981 |
| EP | 0 803 568 A1 | 10/1997 |
| EP | 1301583 B1 | 4/2003 |
| FR | 2502174 A1 | 9/1982 |
| JP | 2004-511331 A | 4/2004 |
| JP | 2004-513621 A | 5/2004 |
| JP | 2005-296905 A | 10/2005 |
| WO | WO 02/06439 * | 1/2002 |

OTHER PUBLICATIONS

Notification of Reason(s) for Refusal mailed Jul. 6, 2010, for JP Application No. 2008-529558, four pages.

Chinese Office Action mailed Mar. 23, 2011, for CN Application No. 200780006221.8, with English Translation, 8 pages.

Notification of Reason(s) For Refusal mailed Mar. 29, 2011, for JP Application No. 2008-554791, with English Translation, four pages.

Chinese Office Action mailed Dec. 24, 2010, for CN Application No. 200680032916.9, with English Translation, 11 pages.

European Search Report mailed Mar. 2, 2011, for EP Application No. 10185759.7, four pages.

Wang, Q. et al. (Feb. 1997). "Influence of Hydraulic Retention Time on Anaerobic Digestion of Pretreated Sludge," *Biotechnol. Tech.* 11(2)105-108.

* cited by examiner

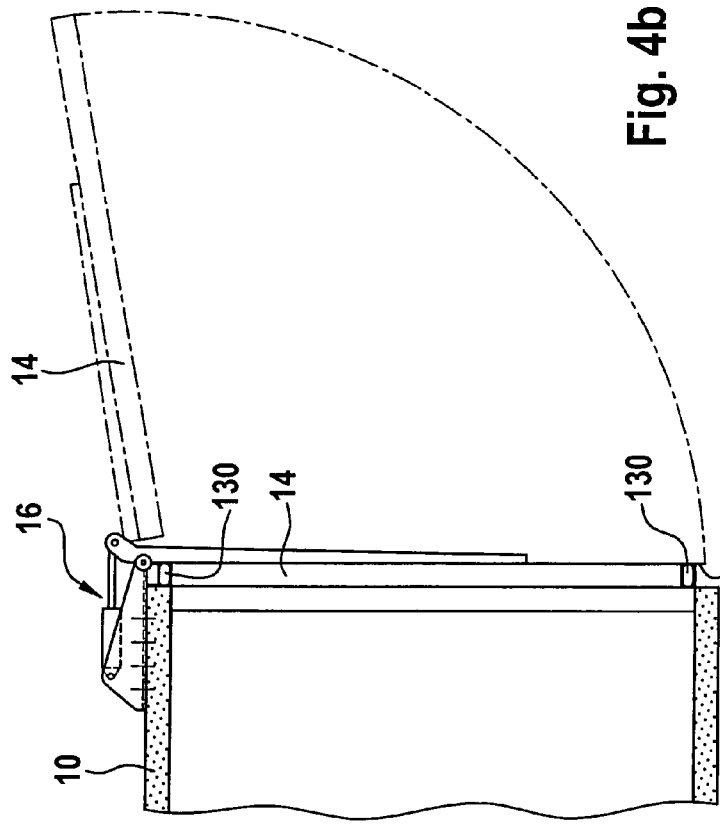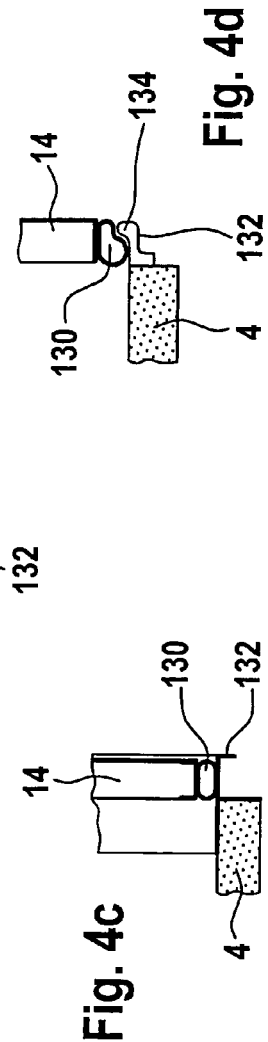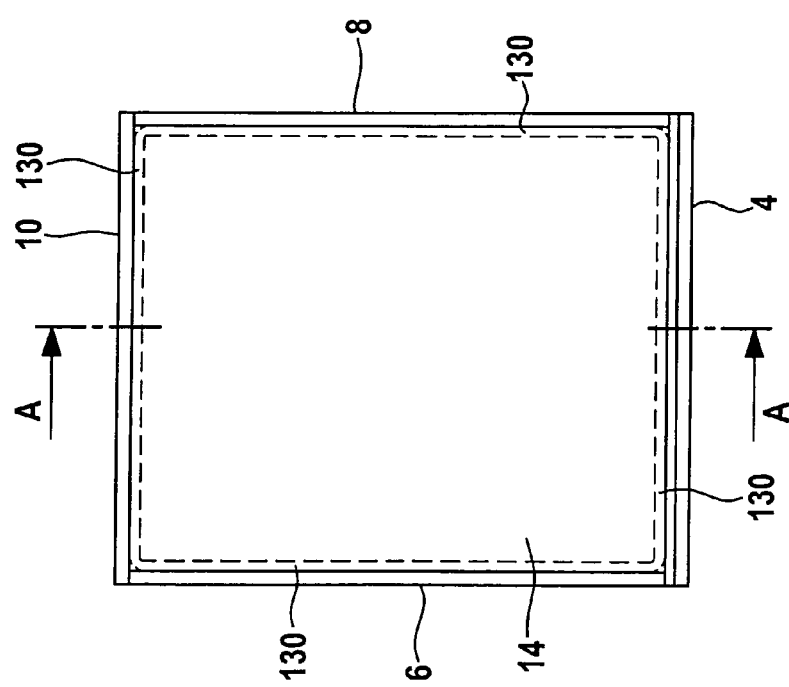

BIOREACTOR COMPRISING A RETAINING SYSTEM

CROSS-REFERENCE TO RELATED APPLICATIONS

This application is a United States National Stage Application under 35 U.S.C. §371 of International Patent Application No. PCT/EP2006/008794, filed Sep. 8, 2006, which claims the benefit to German Patent Application No. 20 2005 014 176.3, filed Sep. 8, 2005, each of which is incorporated by reference into this application as if fully set forth herein.

The invention relates to a bioreactor for the methanation of biomass.

A bioreactor of the type proposed here is known from EP 1 301 583 B1 and, in order to avoid unnecessary repetition, reference is made in full to the disclosure of this prior-art document, the disclosure content of which is expressly incorporated in the present application.

EP 0023176 A2 discloses a bioreactor for the methanation of biomass. This bioreactor comprises a cubic or tubular digester which can be closed in a gas-tight manner by a shutter using an elastic seal. Provided behind the shutter is a skeleton container which is filled with the biomass which is to be fermented. The skeleton container thus provides pressure relief for the gas-tight shutter, and biomass is supported entirely on the skeleton container.

Starting from the bioreactor according to EP-B 1 301 583, the object of the present invention is to improve the known bioreactor to the extent where it can accommodate a large biomass load without adversely affecting the sealing properties of the sealing shutter.

The disadvantage here is that percolate can accumulate between the gas-tight shutter and the retaining system. This percolate can slosh out of the bioreactor as the shutter is opened.

The object of the present invention is thus to improve a known bioreactor to the extent where it is possible to avoid percolate accumulating in the region between the shutter and retaining system.

This object is achieved by a bioreactor as claimed in claim 1.

Using the shutter, which can be closed in a gas-tight manner and is of sufficient dimensions, biomass can easily be introduced into the digester and, following methanation, the residual biomass can easily be removed again. When the digester is closed, the biomass presses substantially, or at least to a certain extent, on the retaining system. The shutter is thus relieved of pressure and may be configured both to be lightweight and to have a precise sealing action. A percolate-drainage system is arranged between the shutter and retaining system, in the floor and/or the walls of the bioreactor. It is thus possible to avoid the accumulation of percolate in the region between the shutter and retaining system and/or prior to the shutter being opened, any percolate located there can be pumped away.

The retaining system is advantageously liquid-permeable. The biomass presses against the retaining system from the inside, under its own dead weight, in which case percolate is squeezed through and out the retaining system, behind which it is collected in the drainage system, arranged in the floor between the retaining system and shutter, and channeled away.

In a preferred embodiment, the retaining system extends from the floor of the digester to a certain way up the same or else, alternatively, over the entire vertical height of the digester. The retaining system may comprise one or more essentially panel-like elements which are inserted into corresponding guide rails. As an alternative, the retaining system can be opened and closed manually or mechanically (pneumatically, hydraulically or the like) by means of hinges, actuators and the like.

The retaining system may, as has been said, comprise essentially one or more vertical panel-like elements. In a first embodiment, these can extend over the entire horizontal width of the digester. In an alternative embodiment, it is also possible for the digester to have, on its end side which can be closed by the shutter, an opening which can be closed by the retaining system and does not extend over the entire width of the digester.

According to an advantageous configuration of the invention, the shutter, which closes off the digester in a gas-tight manner, is provided with an inflatable sealing hose. In the closed state, the sealing hose is inflated and straightforwardly seals the shutter in a gas-tight manner in relation to the digester wall.

According to a further advantageous configuration of the invention, the shutter can be actuated hydraulically since, given corresponding dimensions, it is very difficult to actuate by hand.

According to an advantageous configuration of the invention, the digester is cubic or cuboidal, the shutter forming a wall of the cube or cuboid. This gives rise, on the one hand, to a straightforward construction and, on the other hand, to a sufficiently large opening for loading and filling the digester. In addition, production of the digester is simplified as a result.

According to an advantageous configuration of the invention, the ceiling of the digester can be raised, and closed in a gas-tight manner again, by means of lifting cylinders. This ensures quick ventilation of the digester.

According to an advantageous configuration of the invention, the digester is cylindrical and the shutter is in the form of a discoid cover. This shaping is suitable, in particular, if the biomass is in the form of round straw bales.

According to an advantageous embodiment of the invention, the heating system is integrated in the floor panel of the digester in the manner of a floor-heating system. Since hot gases rise upward, this results in the biomass in the digester being heated uniformly. In addition, or as an alternative, the heating system may also be integrated in the other walls of the digester.

According to a further advantageous configuration of the invention, the digester is constructed in the manner of a prefabricated garage using reinforced concrete. The open side of the "prefabricated garage" is closed in a gas-tight manner by the shutter. This results in a very cost-effective construction.

Further details, features and advantages of the invention can be gathered from the subclaims and from the following description of preferred embodiments. In the drawings:

FIG. 4a shows a plan view of the shutter of the digester;

FIG. 4b shows a sectional illustration of the shutter from FIG. 4a as seen along plane A-A;

FIG. 4c shows a detail of the illustration in FIG. 4b;

FIG. 4d shows a detail-form illustration corresponding to FIG. 4c, but with an alternative configuration of the frame;

Figure 1:
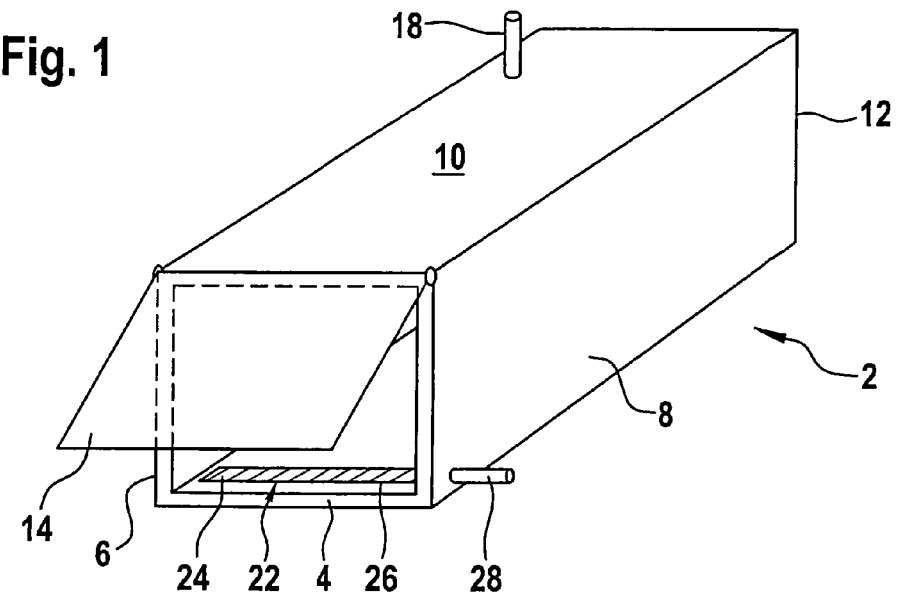
FIG. 1 shows, schematically, a perspective illustration of the bioreactor according to the invention without the retaining system inserted.
Figure 2:
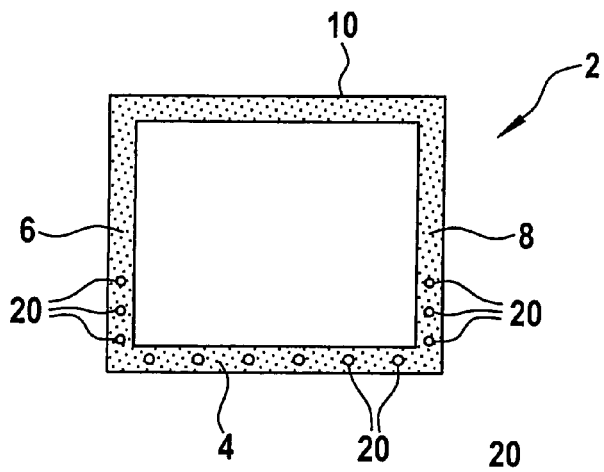
FIG. 2 shows a sectional illustration of the bioreactor according to FIG. 1.
Figure 3:
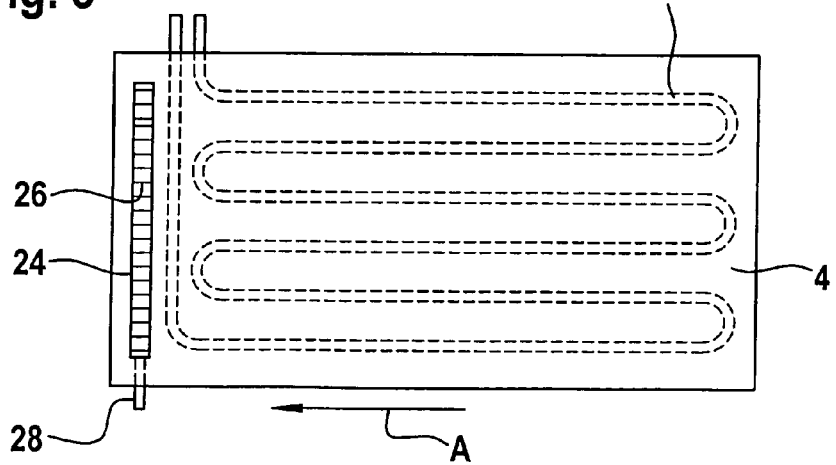
FIG. 3 shows a schematic illustration of the floor panel of the bioreactor from FIGS. 1 and 2.

A bioreactor or biogas reactor according to FIGS. 1 to 3 comprises a cuboidal digester 2 which consists of reinforced concrete, in the manner of a prefabricated garage, and comprises six planar wall elements, namely a floor panel 4, two side walls 6 and 8, a ceiling panel 10, a rear wall 12 and an open front side, which can be closed by a gas-tight shutter 14.

The shutter 14 can be actuated by means of hydraulics 16. When the flap 14 is open, it is easily possible for the digester 2 to be filled and for the residual biomass to be removed therefrom. The biogas generated in the digester 2 is channeled away via a biogas-removal connection 18. A heating system 20 may be provided, in the manner of a floor-heating system, in the floor panel 4 of the digester 2 and, in part, also in the side walls 6 and 8, and can correspondingly temperature-control the biomass located in the digester 2. Also integrated in the floor panel 4 is a percolating-juice-drainage system 22, comprising a traversely running channel 24 which is incorporated in the floor panel 4 and is covered by a perforated or slotted metal sheet 26. A percolating-juice outflow 28 channels away the percolating juice which collects in the channel 24. The floor panel 4 slopes down toward the channel 24, in the direction of the arrow A, in which case the percolating juice can collect in the channel 24.

FIG. 3 illustrates just one channel 24. As an alternative, it is possible to provide a plurality of such channels, which may likewise be arranged transversely or in the longitudinal direction.

FIG. 4a shows a plan view of the digester 2 with the shutter 14 closed. FIG. 4b shows a sectional view of the digester as seen along plane A-A in FIG. 4a, the open shutter 14 being additionally depicted by dashed lines. A sealing hose 130 is fastened all the way round the peripheral region of the shutter 14. In the closed state, the shutter 14 engages in a frame 132—see FIG. 4c—in relation to which the shutter 14 is sealed by virtue of the sealing hose 130 being pumped up to 6 bar.

FIG. 4d shows an alternative configuration of the frame 132, this time with an all-round protrusion 134. As a result of the protrusion 134, the inflated sealing hose 130 engages behind the frame 132, as a result of which the sealing action is further enhanced.

Figure 5:
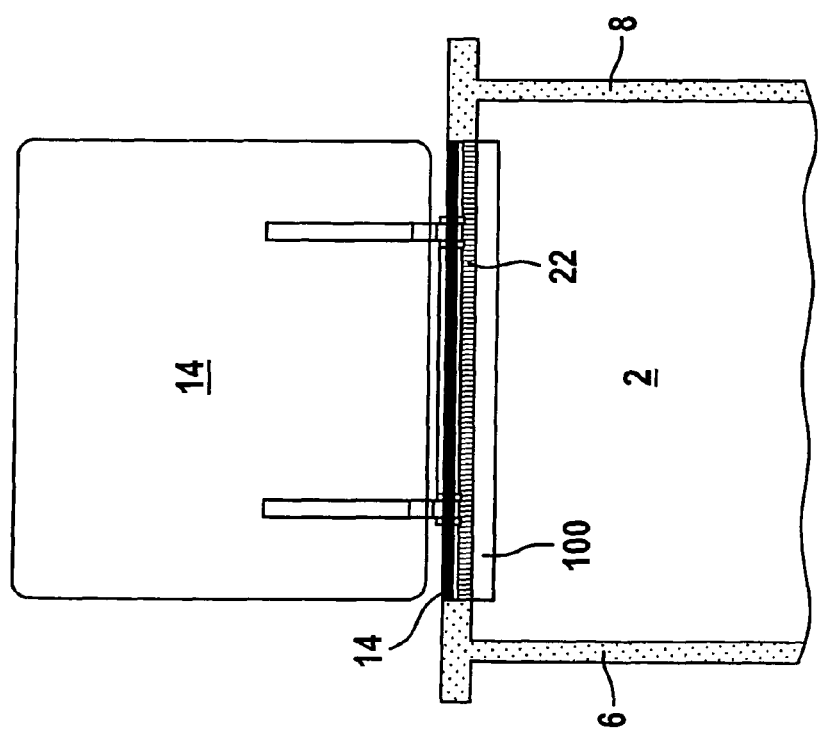
FIG. 5 shows a partial plan view of the bioreactor in the region of the end side which can be closed by the shutter.

FIG. 5 shows a plan view of the front part of the bioreactor with the two side walls 6, 8, the percolating-juice-drainage system 22 and the shutter 14, on the one hand in the closed state (illustrated by dark coloring in FIG. 5) and on the other hand in the swung-up, open state (illustrated by light coloring in FIG. 5). Behind the shutter 14 and the percolating-juice-drainage system 22, as seen in the filling direction, the retaining arrangement 100 is fastened by vertical guide rails by virtue of the panel-like retaining arrangement 100, which is advantageously produced from wood, being introduced into the guide rails from above once the bioreactor has been partially loaded. The bioreactor can then be completely filled through the interspace remaining between the retaining arrangement and the roof of the digester.

In an alternative embodiment which is not shown, it is also possible for the retaining arrangement to be pivoted in the horizontal direction mechanically, for example hydraulically, by means of hinges or to be moved up and down in the vertical direction by means of guide rails.

As can be seen in FIG. 5, it is not necessary for the retaining arrangement 100 to extend over the entire horizontal width of the digester, i.e. from one side wall 6 to the opposite side wall 8. It is also possible for the loading opening, which can be closed by the shutter 14, to be of smaller dimensions, in which case the retaining arrangement may also be designed to be of correspondingly narrower width.

Figure 6:
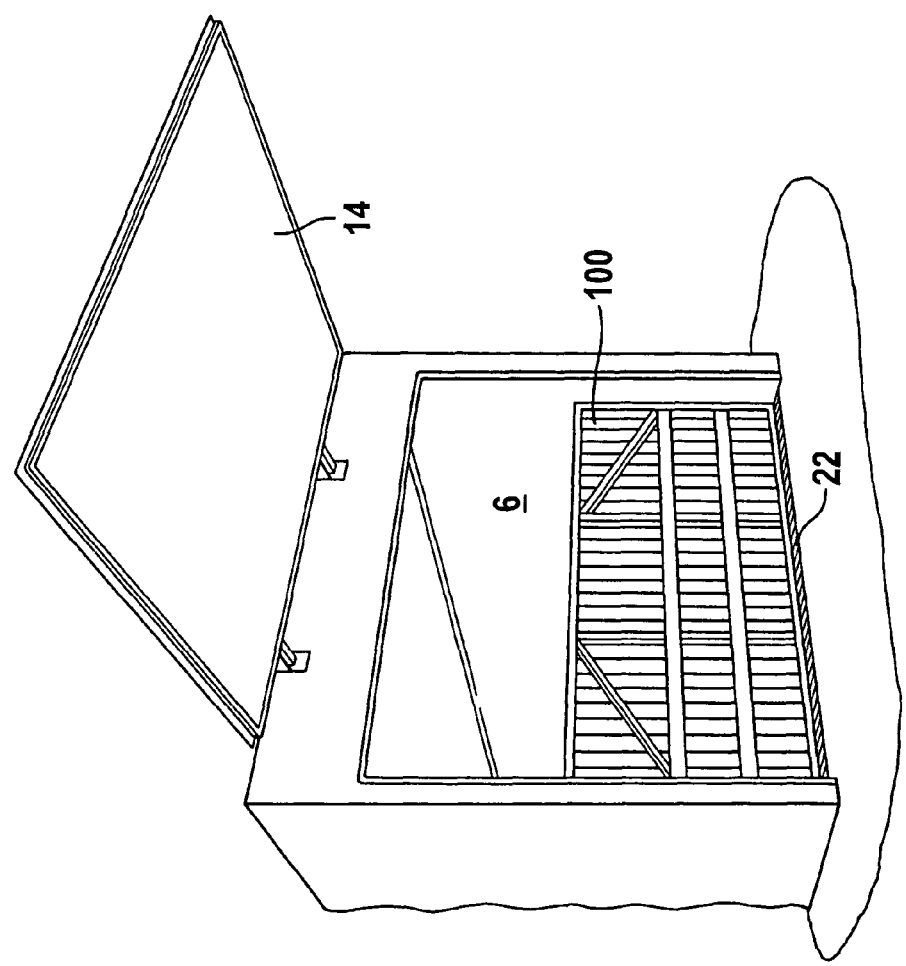
FIG. 6 shows a perspective view of a bioreactor according to the invention with the shutter open and the retaining system inserted.
Figure 7:
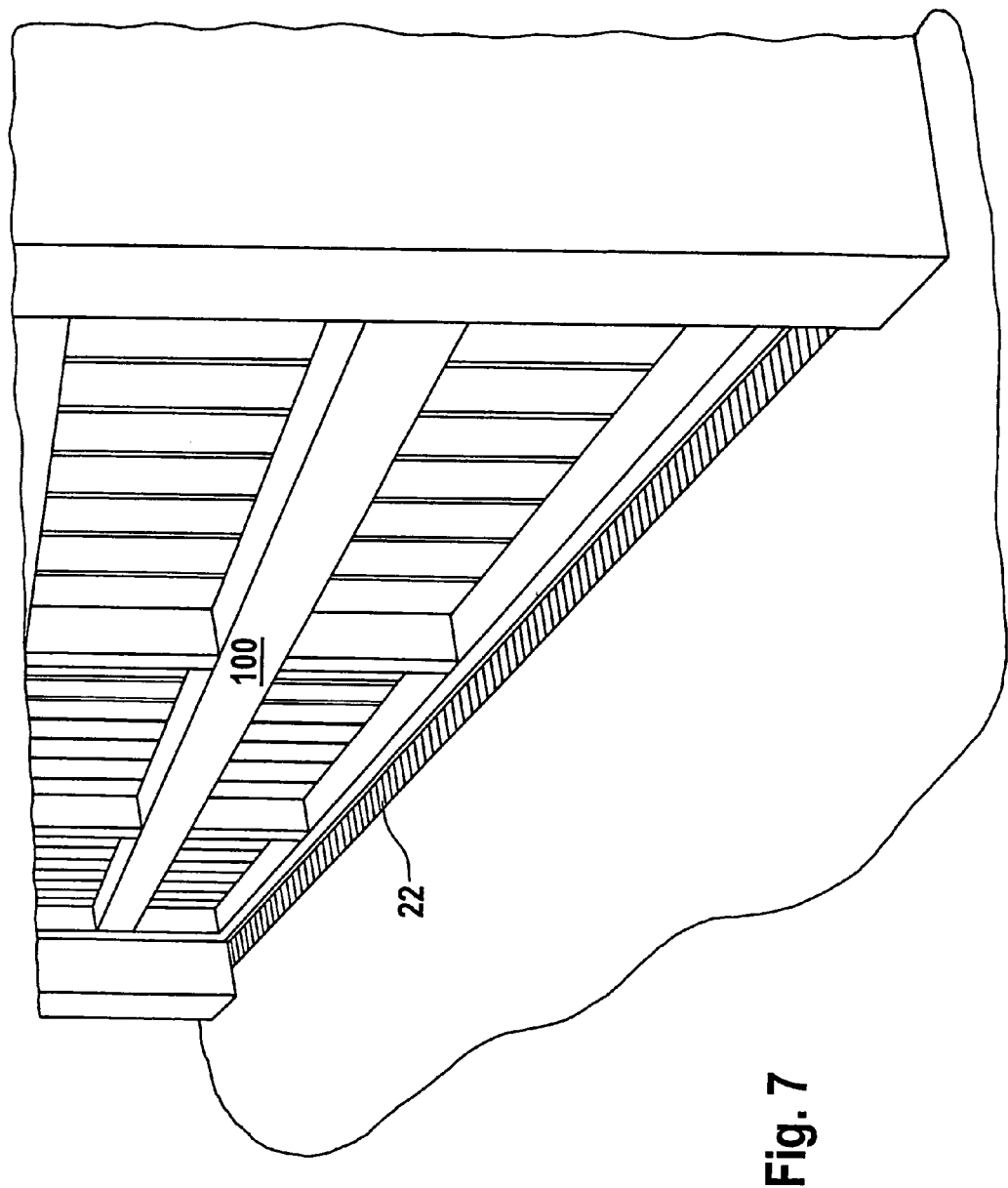
FIG. 7 shows a detail from FIG. 6.

In a further embodiment which is illustrated in FIGS. 6 and 7, in contrast, the retaining arrangement 100 extends over the entire width of the digester.

For loading purposes, the shutter 14 is swung upward, or displaced vertically or horizontally by hydraulic means, and the retaining arrangement is removed by being raised vertically out of the guide rails by, in the embodiment shown here, manual means, for example using a wheeled loader. Thereafter, the digester, for example using wheeled loaders, is partially filled and then the retaining arrangement is reinserted in the reverse order. Filling of the digester can then continue through the interspace that remains at the top between the retaining arrangement 100 and roof of the digester. Finally, the shutter 14 is closed.

The dead weight of the biomass causes percolating juice to be squeezed out of the latter and through the interspaces formed in the retaining arrangement 100. It is advantageously possible for the bioreactor to be loaded with biomass to a more pronounced extent than conventional reactors since the retaining arrangement supports the dead weight. The percolating juice squeezed out in this way collects in the drainage system 22, which, for this purpose, is arranged behind the retaining arrangement 100, as seen from the position of the biomass.

The invention claimed is:

1. A bioreactor for the methanation of solid biomass, comprising:
   a digester intended for accommodating the solid biomass,
   a shutter for loading and unloading the solid biomass and which closes the digester in a gas-tight manner,
   a retaining arrangement which is arranged in the digester, behind the shutter and in front of the solid biomass, as seen from the shutter, such that the solid biomass introduced is supported in part by the retaining arrangement and no solid biomass is accommodated between the shutter and the retaining arrangement, said retaining arrangement is permeable in relation to percolate passing out of the solid biomass and holds back the solid biomass, and
   a percolate drainage system which is arranged in the floor of the digester between shutter and retaining arrangement.

2. The bioreactor of claim 1, characterized in that the retaining arrangement is supported in the digester by guide rails.

3. The bioreactor of claim 1, characterized in that the retaining arrangement extends over the entire width of the digester.

4. The bioreactor of claim 1, characterized in that the retaining arrangement extends only over part of the entire width of the digester, said extending width corresponds to a loading opening which can be closed by the shutter.

* * * * *